United States Patent [19]
Dinger et al.

[11] Patent Number: 6,059,789
[45] Date of Patent: May 9, 2000

[54] DRILL GUIDE FOR CREATING A TUNNEL IN BONE FOR FIXATING SOFT TISSUE TO THE BONE AND KIT AND METHOD FOR FIXATING SOFT TISSUE TO BONE

[75] Inventors: Fred B. Dinger, Jacksonville; Guy K. Williamson, Ponte Vedra Beach, both of Fla.

[73] Assignee: Xomed Surgical Products, Inc., Jacksonville, Fla.

[21] Appl. No.: 09/272,332

[22] Filed: Mar. 19, 1999

Related U.S. Application Data

[60] Provisional application No. 60/090,234, Jun. 22, 1998.

[51] Int. Cl.$^7$ .................................................. A61B 12/56
[52] U.S. Cl. .............................. 606/96; 606/86; 606/80
[58] Field of Search ................................ 606/79, 80, 86, 606/96, 98

[56] References Cited

U.S. PATENT DOCUMENTS

| | | |
|---|---|---|
| 516,294 | 3/1894 | Britton . |
| 2,200,120 | 5/1940 | Nauth . |
| 4,381,770 | 5/1983 | Neufeld . |
| 4,421,112 | 12/1983 | Mains et al. ............................. 606/96 |
| 4,450,835 | 5/1984 | Asnis et al. . |
| 4,622,960 | 11/1986 | Tam . |
| 4,672,957 | 6/1987 | Hourahane . |
| 4,744,353 | 5/1988 | McFarland . |

FOREIGN PATENT DOCUMENTS

| | | |
|---|---|---|
| 3411891 | 10/1985 | Germany . |
| 2147504A | 5/1985 | United Kingdom . |

OTHER PUBLICATIONS

Treatment of Fracture of the Neck of the Femur, E.T. Bailey, M.B. London, Eng., Feb., 1937, pp. 375–376.

"Injuries of the Upper Limb", Fractures and Joint Injuries, vol. II, R. Watson–Jones, 1944.

Campbell's Operative Orthopedics, 5th Edition, vol. I, A.H. Crenshaw, Editor, The C.V. Mosby Company, 1971—St. Louis, MO.

*Primary Examiner*—Michael Buiz
*Assistant Examiner*—Daphna Shai

[57] ABSTRACT

A drill guide for positioning on a surface of a bone includes a projection for penetrating the bone, an abutment for engaging the surface of the bone to ensure penetration of the bone by the projection to a predetermined depth, less than the length of the projection, and a pair of guide passages having central longitudinal axes, respectively, converging at a predetermined point in the bone when the projection penetrates the bone to the predetermined depth. A kit for fixating soft tissue to bone includes a drill guide, a drill bit, a suture and a suture passer. The drill bit is insertable in a pair of guide passages of the drill guide to cut first and second passages converging in the bone to define a continuous tunnel. The suture passer has a portion for being introduced in the tunnel to engage the suture externally of the bone such that the suture is drawn through the tunnel when the suture passer is withdrawn therefrom. A method of fixating soft tissue to bone includes the steps of penetrating a bone with a projection of a drill guide, engaging the bone with an abutment of the drill guide to ensure penetration of the bone by the projection to a predetermined depth, introducing a drill bit through a pair of guide passages of the drill guide and into the bone to form first and second passages converging in the bone to define a continuous tunnel, introducing a suture passer into the tunnel such that a suture engaging member of the suture passer protrudes externally of the bone, engaging a suture with the suture engaging member, withdrawing the suture passer from the tunnel to draw the suture through the tunnel and using the suture to fixate soft tissue to the bone.

20 Claims, 5 Drawing Sheets

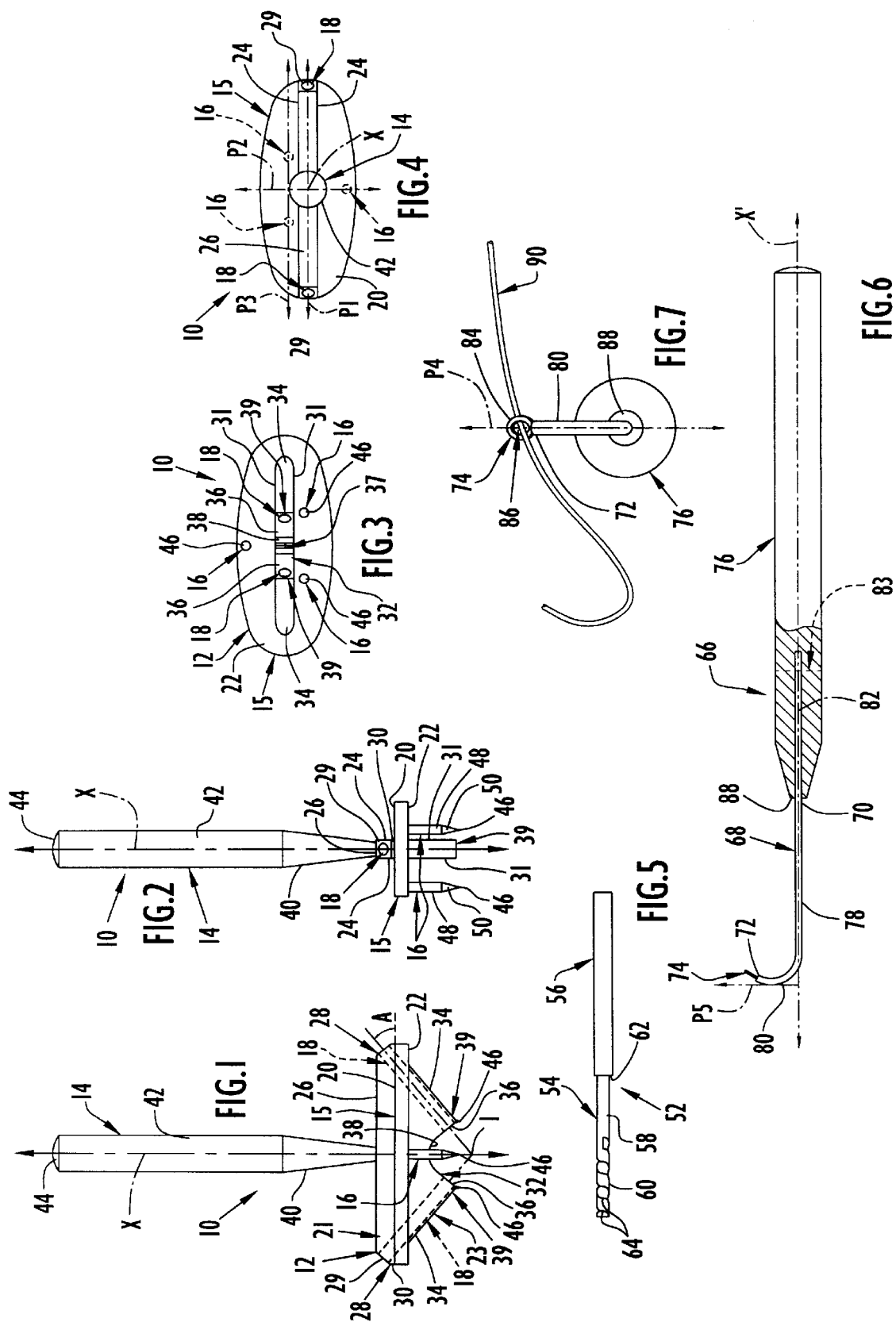

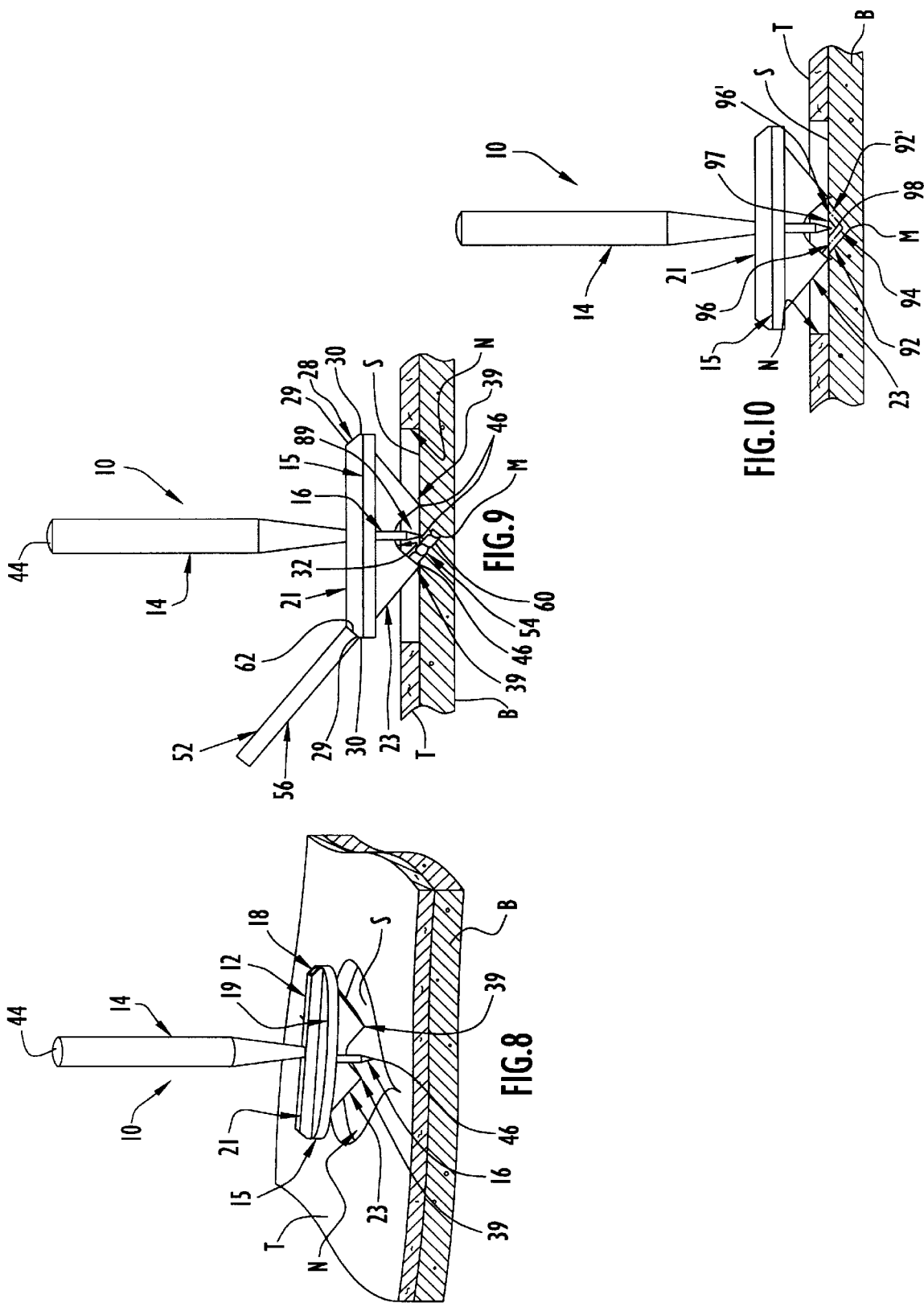

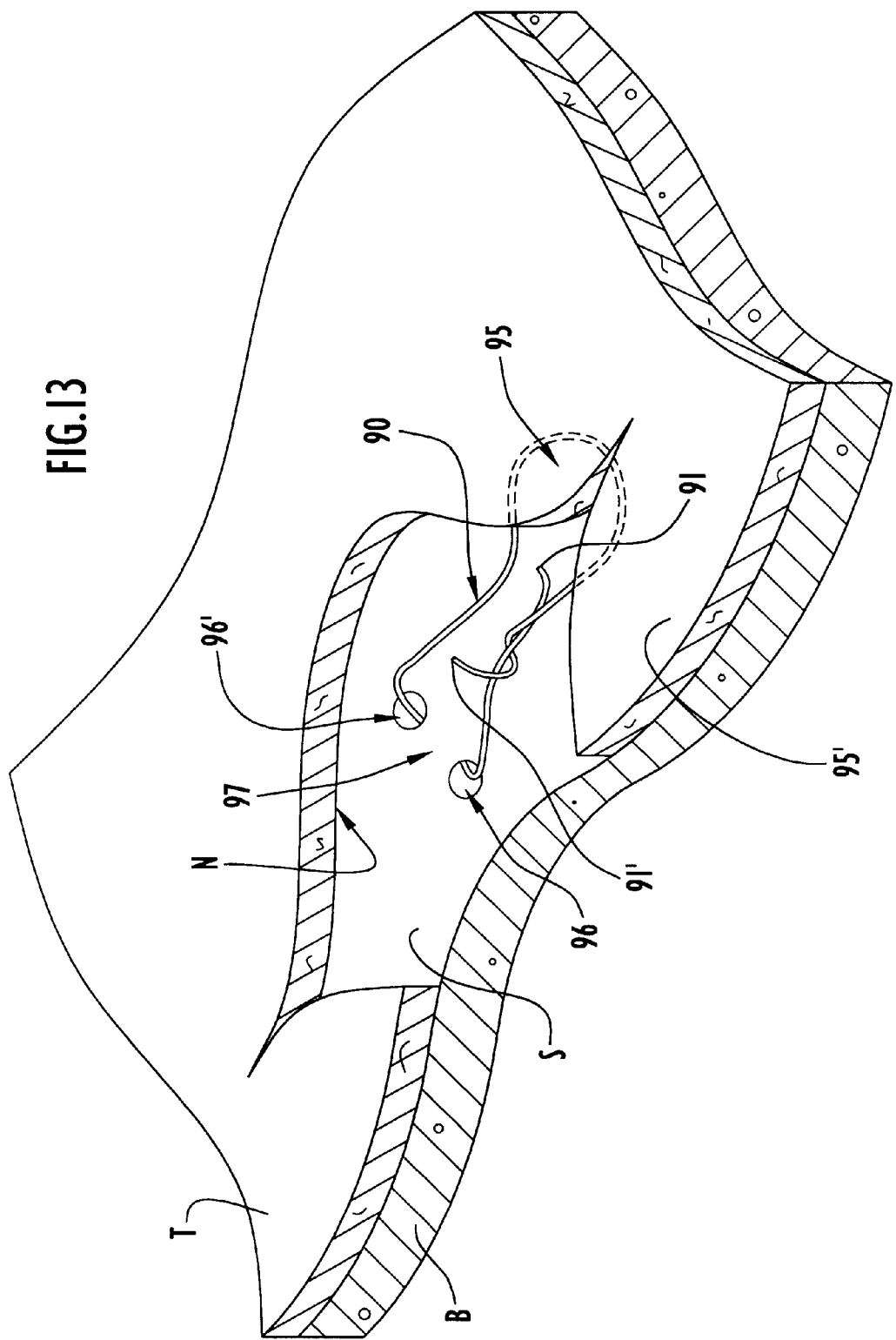

DRILL GUIDE FOR CREATING A TUNNEL IN BONE FOR FIXATING SOFT TISSUE TO THE BONE AND KIT AND METHOD FOR FIXATING SOFT TISSUE TO BONE

CROSS REFERENCE TO RELATED PATENT APPLICATION

This application claims priority from provisional patent application Ser. No. 60/090,234 filed Jun. 22, 1998, the disclosure of which is incorporated herein by reference.

BACKGROUND OF THE INVENTION

1. Field of the Invention

The present invention relates to fixation of soft anatomical tissue to bone and, more particularly, to a drill guide for use in forming a tunnel in bone used to secure soft anatomical tissue to the bone and to a kit and method for fixating soft anatomical tissue to bone.

2. Discussion of the Related Art

Various surgical procedures require the fixation of soft anatomical tissue, such as ligaments, tendons, muscles, fascia, cartilage, connective tissue and layers of the skin, to bone. Many of the devices and techniques that have been proposed for fixating soft tissue to bone have demonstrated unreliable fixation and add considerably to the cost of surgery. Screws or anchors typically used for fixating soft tissue to bone are expensive and present the additional drawback of requiring that they either be left in place permanently or be removed subsequent to healing. Many patients are uncomfortable with the prospect of permanent implants as well as with the alternative prospect of later removal of fixation devices. Although bioabsorbable fixation devices have been proposed, such devices are considerably more expensive.

Fixating tissue to bone via a suture or wire passed through a tunnel formed in the bone has also been proposed. Illustrative instruments and methods for fixating tissue to bone using a suture or wire passed through a bone tunnel are disclosed in U.S. Pat. No. 4,672,957 to Hourahane and U.S. Pat. No. 4,744,353 to McFarland, which disclose instruments and methods for suturing soft tissue to bone, and in U.S. Pat. No. 4,622,960 to Tam, which discloses wiring a bone section to another bone section. A major disadvantage of prior procedures for suturing or wiring tissue to bone is that the suture or wire is inserted in the bone tunnel and is engaged, within the bone tunnel, by an engaging member used to draw the suture or wire entirely through the bone tunnel. Since visibility inside the bone tunnel is limited and typically obstructed, engagement of the suture or wire within the bone tunnel must be done by feel or "fishing" and is time consuming and tedious. The Hourahane and McFarland patents disclose drill guides for guiding drills to form intersecting passages in the bone defining a bone tunnel. However, there is no structural cooperation between the drill guides and the drills to limit or control the depth of insertion of the drills in the bone such that more bone than necessary is typically removed. Furthermore, the drill guide disclosed by Hourahane has pins disposed entirely within the bone during use. Accordingly, significant force must be applied to the drill guide to cause the pins to fully enter the bone, and bone must be displaced by the pins. In addition, the prior devices and methods do not recognize the significance of forming a bone tunnel to a shallow predetermined depth in bone for cooperation with a suture passer that, when introduced in an access opening of the bone tunnel, protrudes externally from the bone tunnel to engage a suture externally of the bone.

Accordingly, the need exists for a reliable and effective technique for fixating soft anatomical tissue to bone or other similar tissue without the need for permanent implants or the subsequent removal of fixation devices while being cost effective, safe for the patient and easy to execute by surgeons. A particular need exists for apparatus and a method for suturing soft tissue to bone via a suture passed through a shallow tunnel in the bone by a suture passer that engages the suture externally of the bone. The need also exists for apparatus and a method for forming a tunnel in bone to a shallow predetermined depth while minimizing the amount of bone removed and the force applied to the bone.

OBJECTS AND SUMMARY OF THE INVENTION

Accordingly, it is a primary object of the present invention to overcome the aforementioned drawbacks of conventional devices and techniques for fixating soft tissue to bone.

Another object of the present invention is to form a tunnel in bone to a shallow predetermined depth, to introduce a suture passer through a first access opening of the tunnel so that a distal end of the suture passer protrudes externally from the tunnel through a second access opening thereof and to engage a suture externally of the bone with the distal end of the suture passer such that the suture is drawn through the tunnel when the suture passer is withdrawn through the first access opening.

It is also an object of the present invention to use a drill bit to drill converging passages in a bone to form a continuous tunnel in the bone and to limit penetration of the drill bit into the bone to a predetermined depth so that no more bone than necessary is removed.

Another object of the present invention is to penetrate bone with a projection of a drill guide positioned upon a surface of the bone and to engage the bone surface with an abutment of the drill guide to ensure penetration of the bone by the projection to a predetermined depth such that only a portion of the projection penetrates the bone to minimize the amount of bone displaced and the force required to penetrate the bone.

A further object of the present invention is to limit penetration of a bone by a projection of a drill guide positioned upon a surface of the bone such that longitudinal axes of a pair of guide passages, respectively, of the drill guide converge at a predetermined point in the bone.

It is also an object of the present invention to limit penetration of a bone by a projection of a drill guide positioned upon a surface of the bone such that longitudinal axes of a pair of guide passages, respectively, of the drill guide converge within the bone and to limit the distance to which a drill bit may be introduced in the guide passages and into the bone such that first and second passages formed in the bone with the drill bit terminate and converge at a predetermined point of maximum depth in the bone.

Yet another object of the present invention is to limit the depth to which a drill bit can be introduced in a pair of guide passages, respectively, extending angularly through a drill guide positioned on a surface of a bone such that the drill bit is guided by the guide passages to form first and second passages, terminating a predetermined depth in the bone, such that longitudinal axes of the first and second passages, respectively, intersect at a predetermined point in the bone.

It is also an object of the present invention to drill converging passages in a bone to form a continuous tunnel in the bone, to introduce a portion of a suture passer in the tunnel, to engage a suture with the suture passer externally of the bone, to draw the suture through the bone tunnel with the suture passer portion and to suture soft tissue to the bone utilizing the suture.

Some of the advantages of the present invention are that a tunnel is accurately formed in bone to a point of maximum predetermined depth, formation of the tunnel results in creation of a bone bridge to which the soft tissue is fixated by the suture, the guide passages extend through a ridge member and an abutment member above and below a support plate of the drill guide for enhanced support and guidance of the drill bit, the drill bit can be designed as a "universal" component for being coupled with conventional powered handpieces, the drill guide is held in place and stabilized on the bone due to penetration of the bone by at least one projection and due to engagement of the abutment member with the bone surface, the at least one projection need only penetrate the bone a small amount to minimize bone displacement and the force needed to penetrate the bone with the at least one projection, the drill bit is prevented from "overshooting" the point of maximum depth such that the amount of bone removed is kept to a minimum, the need for blind "fishing" for a suture with a suture passer is eliminated, soft tissue is fixated to bone without the need for temporary or permanent mechanical fixation devices, soft tissue can be fixated to bone with desired tension, soft tissue can be elevated and fixated to bone to maintain the elevated position of the soft tissue as is particularly useful in cosmetic surgery, the present invention can be used in many areas of surgery, and soft tissue can be reliably and effectively fixated while reducing surgical cost.

These and other objects, advantages and benefits are achieved with the present invention as generally characterized in a drill guide for positioning upon a surface of a bone and comprising a support plate, an abutment member protruding below the support plate and terminating at at least one contact point forming an abutment with the surface of the bone when the drill guide is positioned thereon, at least one projection extending from the support plate and terminating at a tip disposed a distance below the support plate for penetrating the bone and a pair of guide passages extending angularly through the drill guide for receiving and guiding a drill bit. The at least one contact point is disposed a distance below the support plate that is less than the distance that the tip of the at least one projection is disposed below the support plate. Accordingly, when the drill guide is positioned upon a surface of a bone and the bone is penetrated with the tip of the at least one projection, the at least one contact point engages the surface of the bone when the at least one projection has penetrated the bone to a predetermined depth. Engagement of the at least one contact point with the surface of the bone limits further penetration of the bone by the at least one projection, such that only a portion of the at least one projection is disposed in the bone. The guide passages have central longitudinal axes, respectively, that converge at a predetermined point of convergence within the bone when the at least one projection penetrates the bone to the predetermined depth such that a drill bit guided into the bone by the guide passages forms converging passages in the bone defining a continuous tunnel in the bone. It should be appreciated that, as used herein, "bone" is intended to include bone as well as any other anatomical tissue similar to and/or having the characteristics of bone, such as dense, hard, ossiferous or calcified tissue referred to herein as "bony" or "bone-like" tissue.

A kit or system for fixating soft tissue to bone according to the present invention includes a drill guide, a drill bit, a suture and a suture passer. The drill guide includes a support plate, an abutment member terminating below the support plate at at least one contact point forming an abutment with a surface of the bone when the drill guide is positioned thereon, a pair of angularly extending guide passages and at least one projection extending from the support plate to terminate at a tip disposed a distance below the support plate for penetrating the bone when the drill guide is disposed upon the surface of the bone. The at least one contact point is disposed a distance below the support plate that is less than the distance that the tip of the at least one projection is disposed below the support plate such that the abutment member limits penetration of the bone by the at least one projection to a predetermined depth. The guide passages have central longitudinal axes, respectively, converging at a predetermined point of convergence within the bone when the at least one projection penetrates the bone to the predetermined depth. The drill bit includes a cutting member for being introduced in the guide passages and for being moved forwardly in the guide passages and into the bone to cut converging passages in the bone forming a continuous tunnel in the bone and having access openings, respectively, on the surface of the bone. The suture includes a length of filamentous suture material having opposing ends. The suture passer has a portion for being introduced in the tunnel through one of the access openings such that a suture engaging member of the suture passer protrudes from the other access opening externally of the bone to engage the suture. The suture passer is withdrawable from the tunnel through the one access opening to draw the suture through the tunnel such that the opposing ends extend externally from the access openings, respectively, for suturing soft tissue to the bone.

A method of fixating soft tissue to bone according to the present invention includes the steps of positioning a drill guide upon a surface of a bone, penetrating the bone with a tip of at least one projection of the drill guide, engaging the bone with an abutment of the drill guide to ensure penetration of the bone by the at least one projection to a predetermined depth such that central longitudinal axes of angularly extending guide passages, respectively, of the drill guide converge at a predetermined point of convergence within the bone, introducing a drill bit through the guide passages and into the bone to form first and second angled passages, respectively, converging in the bone to define a continuous tunnel in the bone and having access openings, respectively, on the surface of the bone, introducing a portion of a suture passer into the tunnel through one of the access openings such that a suture engaging member of the suture passer protrudes externally from the other access opening, engaging a length of suture material with the suture engaging member externally of the surface of the bone, withdrawing the suture passer through the one access opening to draw the length of suture material through the tunnel such that opposing ends of the length of suture material extend externally from the access openings, respectively, passing one of the ends of the length of suture material through soft tissue and tying the ends of the length of suture material to fixate the soft tissue to the bone. These and other objects, advantages and benefits of the present invention will become apparent from the following description of the preferred embodiments taken in conjunction with the accompanying drawings herein like parts in each of several figures are identified by the same reference numerals.

BRIEF DESCRIPTION OF THE DRAWINGS

FIG. 1 is a front view of a drill guide according to the present invention.

FIG. 2 is a side view of the drill guide.

FIG. 3 is a bottom view of the drill guide.

FIG. 4 is a top view of the drill guide.

FIG. 5 is a side view of a drill bit for use with the drill guide to drill converging passages in bone forming a continuous tunnel in the bone.

FIG. 6 is a side view, partly in section, of a suture passer for use in passing a suture through the tunnel formed with the drill guide and drill bit.

FIG. 7 is an end view of the suture passer engaging a suture.

FIG. 8 is a broken, perspective view, partly in section, illustrating the drill guide positioned on a surface of a bone accessed via an incision in soft tissue.

FIG. 9 is a broken view, partly in section, showing projections of the drill guide penetrating the bone to a predetermined depth and illustrating use of the drill guide and the drill bit to form converging passages in the bone.

FIG. 10 is a broken view, partly in section, illustrating a continuous tunnel in the bone formed by the converging passages and a bone bridge created in the bone between access openings of the tunnel.

FIG. 13 is a broken, perspective view, partly in section, illustrating passage of the suture through the soft tissue and tying of the ends of the suture.

DESCRIPTION OF THE PREFERRED EMBODIMENTS

Figure 14:
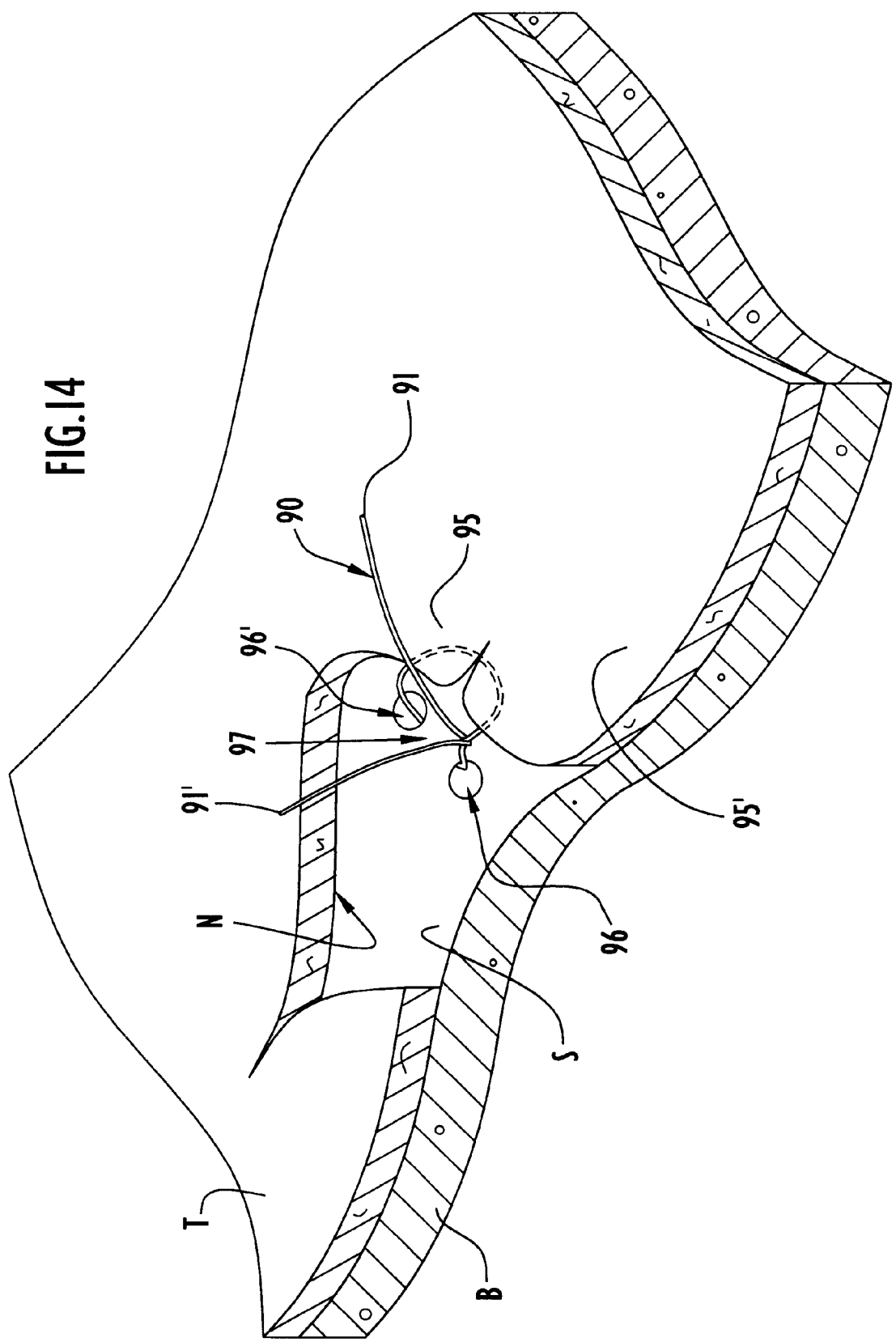
FIG. 14 is a broken, perspective view, partly in section, illustrating tightening of the suture to elevate the soft tissue and fixate the elevated soft tissue to the bone with desired tension.

A drill guide 10 according to the present invention is illustrated in FIGS. 14 and includes a guide member 12 and a handle 14 mounted to guide member 12. Guide member 12 includes a support plate 15, projections, posts or spikes 16 protruding downwardly from support plate 15 a ridge member 21 protruding upwardly from support plate 15, an arch or abutment member 23 protruding downwardly from support plate 15 and guide passages 18 extending angularly through ridge member 21, support plate 15 and arch member 23. Support plate 15 is flat or planar and has an oval or oblong peripheral configuration as shown in FIGS. 3 and 4 with a uniform or constant thickness between a planar upper surface 20 and a planar lower surface 22. The support plate 15 has a major length contained in a plane P1 and a major width contained in a plane P2 perpendicular to the plane P1 as shown in FIG. 4. The ridge member 21 protrudes upwardly from upper surface 20, and the arch member 23 protrudes downwardly from lower surface 22. The ridge member 21 extends the entire major length of support plate 15 and is defined by a pair of planar, parallel side walls 24, a planar top wall 26 and a pair of end walls 28. The side walls 24 are perpendicular to upper surface 20 and parallel to plane P1. The top wall 26 is perpendicular to side walls 24 and parallel to upper surface 20. Each end wall 28 includes a planar, angled or chamfered end wall segment 9 angled downwardly and outwardly from the top wall 26 and an end wall segment 30 extending downwardly from the angled end wall segment 29 to meet or merge with a peripheral edge of support plate 15. Planes P1 and P2 intersect at a central axis X of support plate 15, which is also the central axis of guide member 12. The ridge member 21 is symmetrical relative to the central axis X with plane P1 centrally disposed between side walls 24 and plane P2 centrally disposed between end walls 28.

The arch or abutment member 23 extends less than the entire major length of support plate 15 and is defined by a pair of planar, parallel side walls 31, a curved bottom wall 32 and a pair of planar, angled end walls 34. The side walls 31 are perpendicular to lower surface 22 and are disposed in the same planes, respectively, as side walls 24. The end walls 34 are angled upwardly and outwardly from the bottom wall 32 to meet or merge with the lower surface 22 inwardly of the peripheral edge of support plate 15. The bottom wall 32 includes planar end segments 36 and a curved intermediate segment 38 between planar end segments 36. The end segments 36 are parallel to end wall segments 29, and the intermediate segment 38 curves upwardly and inwardly from the end segments 36. The arch member 23 is symmetrical relative to the central axis X with plane P1 centrally disposed between side walls 31 and plane P2 centrally disposed between end walls 34 such that the bottom wall 32 is bisected by plane P2 and, therefore, is bisected by the central axis X. The bottom wall 32 is bisected by the central axis X at an uppermost point 37 defining a minimum perpendicular distance for arch member 23 below or beneath the plane of lower surface 22. The end segments 36 meet the end walls 34, respectively, at lowermost points or lowermost ends 39, respectively, which define a predetermined, maximum perpendicular distance for arch member 23 below or beneath the plane of lower surface 22. The lowermost ends or points 39 are contact points forming an abutment with a surface of bone as explained further below. It should be appreciated that one or more lowermost ends or contact points may be provided on guide member 12 depending on the configuration of the arch or abutment member 23. The guide member 12 is preferably made of a strong material such as 174 H900 stainless steel.

According to a preferred embodiment, the major length of the support plate 15 is in the range of 1.495 to 1.505 inches and, preferably, 1.500 inches, the major width of the support plate 15 is in the range of 0.639 to 0.649 inch and, preferably, 0.644 inch, and the thickness of the support plate 15 between upper surface 20 and lower surface 22 is in the range of 0.089 to 0.091 inch and, preferably, 0.090 inch. The length of top wall 26 is preferably 1.338 inches. The thickness of ridge member 21 between side walls 24 is preferably 0.125 inch. The height of ridge member 21 between top wall 26 and upper surface 20 is preferably 0.125 inch. The thickness of arch member 23 between side walls 31 is preferably 0.125 inch. The perpendicular distance between the planes of end wall segments 29, respectively, and the planes of end segments 36, respectively, is 0.686 to 0.690 inch and, preferably, 0.687 inch. The perpendicular predetermined distance from lower surface 22 to lowermost points 39 is 0.321 to 0.325 inch and, preferably, 0.323 inch. The distance between lowermost points 39 perpendicular to plane P2 is 0.445 to 0.449 inch and, preferably, 0.447 inch. The radius of curvature of intermediate segment 38 is preferably 0.125 inch.

Handle 14 is centrally located on guide member 12 and extends perpendicularly from top wall 26. Handle 14 includes a truncated conical neck 40 attached to ridge member 21 and merging with an elongate, cylindrical body 42 terminating at a rounded end 44. Handle 14 has a central longitudinal axis coincident or coaxial with the central axis X as shown in FIGS. 1, 2 and 4. The cylindrical body 42 preferably has a knurled outer or external surface to facilitate grasping of handle 14. Handle 14 can be attached to guide member 12 in various ways. For example, neck 40 may be provided with an extension for securement in a recess, passage or hole in ridge member 21 with the extension being secured in such recess, passage or hole via threads, welding, adhesives, heat bonding, mechanical securing elements or any other suitable securing means. According to a preferred embodiment, the cylindrical body 42 has a diameter of 0.25 inch, the length of handle 14 extending from top wall 26 is 1.888 to 1.932 inches and, preferably, 1.875 inches, and the handle 14 is provided with an externally threaded extension 0.088 to 0.092 inch long and, preferably, 0.090 inch long and 0.120 to 0.130 inch in diameter and, preferably, 0.125 inch in diameter for being threadedly received in an internally threaded passage of ridge member 21.

Projections 16 extend perpendicularly from lower surface 22 to terminate at sharp tips or points 46 as shown in FIGS. 1 and 2. The drill guide 10 has three projections 16 arranged around the central axis X; however, the drill guide can have one or more projections depending on the size and/or configuration of the support plate. As shown in FIG. 2, each projection 16 has a cylindrical segment 48 and a tapered or conical segment 50 extending downwardly from the cylindrical segment 48 and terminating at the corresponding sharp tip or point 46. Each projection 16 has a central longitudinal axis perpendicular to lower surface 22, and the tips 46 are aligned with the central longitudinal axes, respectively, of projections 16. The sharp tips or points 46 are capable of penetrating bone or bony or bone-like tissue. The projections 16 are arranged in a triangular pattern around the central axis X as shown in FIGS. 3 and 4. As shown in FIG. 4, one projection 16 has its central longitudinal axis contained or located in plane P2. The other two projections 16 have their central longitudinal axes, respectively, contained or located in a plane P3 perpendicular to plane P2 and parallel to plane P1. The projection 16 contained in plane P2 is spaced from and is disposed on one side of plane P1 while the projections 16 contained in plane P3 are spaced from and are disposed on an opposite side of plane P1. One of the projections contained in plane P3 is disposed on one side of plane P2 while the other projection contained in plane P3 is disposed on an opposite side of plane P2. The length of projections 16 from the lower surface 22 to the tips 46 defines a predetermined, maximum perpendicular distance for projections 16 below or beneath the support plate 15. According to a preferred embodiment, the projections 16 each have a length from lower surface 22 to tips 46 of 0.335 to 0.341 inch and, preferably, 0.338 inch, the cylindrical segments 48 each have a diameter of 0.122 to 0.128 inch, and, preferably 0.125 inch, the tapered segments 50 each define an angle of 43° to 47° and, preferably, 45° at tips 46, the perpendicular distance from plane P1 to the central longitudinal axis of the projection 16 contained in plane P2 is 0.260 inch, the perpendicular distance from plane P1 to plane P3 is 0.157 inch, and the central longitudinal axes of the projections 16, respectively, contained in plane P3 are each located a perpendicular distance of 0.245 inch from plane P2.

Guide passages 18 extend entirely through the guide member 12 at an angle to the central axis X, the guide passages 18 each extending through the ridge member 21, the support plate 15 and the arch member 23. Guide passages 18 have entry openings on end wall segments 29, respectively, as shown in FIG. 4, exit openings on end segments 36 as shown in FIG. 3 and central longitudinal axes, respectively. The central longitudinal axes of the guide passages 18 are contained or located in plane P1 and are parallel to end walls 34, respectively. As shown in FIG. 1, the central longitudinal axes of the guide passages 18, respectively, are disposed at an angle A of 39.5 to 40.5 and, preferably, 40, to the plane of upper surface 20. The guide passages 18 are angled toward one another such that their central longitudinal axes converge at a point of convergence I disposed below or beneath the lowermost points or ends 39 as shown in FIG. 1, the point of convergence I being aligned or coincident with the central axis X. The length of the guide passages 18 corresponds to the perpendicular distance between the planes of end wall segments 29 and the planes of end segments 36. According to a preferred embodiment, the length of the guide passages 18 is 0.686 to 0.690 inch and, preferably, 0.687 inch, the diameter of the guide passages 18 is 0.082 to 0.083 inch and, preferably, 0.082 inch, and the perpendicular distance from end walls 34 to the central longitudinal axes of the guide passages 18, respectively, is 0.061 to 0.063 inch and, preferably 0.062 inch.

The predetermined, maximum perpendicular distance of arch member 23 below the support plate 15, i.e. the perpendicular distance from the plane of lower surface 2 to lowermost points or lowermost ends 39, is slightly less than the predetermined, maximum perpendicular distance of projections 16 below the support plate 15, i.e. the perpendicular distance from the plane of lower surface 22 to tips 46, such that the arch member 23 forms a stop or abutment controlling the depth to which the projections 16 penetrate bone when the guide member 12 is disposed upon a surface of the bone as described further below. In particular, engagement, contact or abutment of the contact points 39 of arch member 23 with the surface of the bone limits or ensures penetration of the bone by the projections 16 to a predetermined depth such that only a portion of each projection 16 penetrates the bone. According to the preferred embodiment, the predetermined perpendicular distance between the plane of lower surface 22 and lowermost ends or contact points 39 is less than 0.335 inch and, preferably, is 0321 to 0.325 inch and, preferably, 0.323 inch. Accordingly, when the drill guide 10 is placed on a surface of bone, the projections 16 penetrate the bone to a predetermined depth of 0.010 to 0.020 inch and, preferably, 0.015 inch before the lowermost ends or contact points 39 engage the bone surface and prevent further penetration of the bone by the projections 16. Only a small amount of penetration of the bone surface by the projections 16 is sufficient to stabilize the drill guide 10 on the bone surface and deter displacement of the drill guide 10 during use. Accordingly, only a small amount of bone is displaced or lost due to penetration of the bone by the projections to the predetermined depth. In addition, engagement of the lowermost ends or contact points of the arch member with the bone surface when the projections penetrate the bone to the predetermined depth further stabilizes the drill guide on the bone surface during use. When the contact points 39 engage the bone surface, the support plate 15 is disposed above and is spaced from the bone surface, the support plate 15 being supported by arch member 23. The contact points 39 in engagement with the bone surface at discrete points provides greater stability for the drill guide, particularly where the bone surface is non-planar, since the bone surface does not have to be engaged by the relatively larger, planar lower surface of support plate 15. When the drill guide 10 is disposed on the bone surface with the bone penetrated by projections 16 to the predetermined depth, the point of convergence I will be disposed a predetermined depth within the bone, i.e. below or beneath the bone surface upon which the drill guide 10 is disposed, and the drill guide 10 will be ready for use in forming converging passages in the bone to form a continuous tunnel in the bone and a bone bridge as explained further below.

FIG. 5 illustrates a drill bit 52 for use with the drill guide 10 to drill converging passages in bone forming a continuous tunnel in the bone in accordance with the present invention. The drill bit 52 includes an elongate cutting member 54 for being received in the guide passages 18 and an elongate cylindrical shaft 56 coupled with or unitarily, integrally formed with the cutting member 54. Cylindrical shaft 56 is capable of being coupled with a conventional powered handpiece (not shown) for rotatably driving the drill bit 52 in a conventional manner. The drill bit 52 is preferably designed as a "universal" component to be coupled with various standard powered handpieces currently available, and the shaft 56 can easily be modified, as necessary, to be received by various specialized or customized powered handpieces. The cutting member 54 includes a smooth, cylindrical segment 58 joined to shaft 56 and a fluted segment 60 extending distally from cylindrical segment 58. The cylindrical segment 58 has an external diameter smaller than the external diameter of shaft 56 such that a shoulder 62 is defined at the junction of shaft 56 and cylindrical segment 58, the shoulder 62 forming a stop or abutment limiting the distance or depth to which the cutting member 54 may be inserted in the guide passages 18 to a maximum predetermined distance or depth as explained further below. Two helical flutes are formed on fluted segment 60 forming longitudinally extending helical cutting edges 64 for forming a cylindrical passage or bore in bone when the cutting member 54 is rotated and is advanced distally or forwardly in the bone. According to a preferred embodiment, the shaft 56 has an external diameter of 0.120 to 0.126 inch and, preferably, 0.123 inch, the shaft 56 has a length of 1.25 inches, the cutting member 54 has an external diameter of 0.080 to 0.081 inch and, preferably, 0.081 inch for forming a corresponding diametrically sized passage in bone, the cutting member 54 has a length 20 of 0.957 inch to 0.962 inch and, preferably, 0.962 inch, the fluted segment 60 has a length 21 of 0.50 inch, the shoulder 62 is planar and perpendicular to a longitudinal axis of the drill bit, and the drill bit is made of 440A stainless steel with a hardness in the range of Rc54-56.

A suture passer 66 for use in passing or drawing a suture through a tunnel formed in bone with the drill guide 10 and drill bit 52 is illustrated in FIGS. 6 and 7. The suture passer 66 includes an elongate shaft 68 having a proximal end 70 and a distal end 72, a suture engaging member 74 disposed at the distal end 72 and a handle 76 mounted to the proximal end 70. The shaft 68 has a straight proximal portion 78 and a curved distal portion 80 terminating at distal end 72. The proximal end 70 of shaft 68 is secured to handle 76, such as by having a proximal extension 82 thereof received in a passage or channel formed in the handle 76. The proximal extension 82 can be secured in the passage or channel of handle 76 in various ways including the use of securing members or detents, such as one or more pins 83 (shown in dotted lines in FIG. 6) extending through handle 76 transverse or perpendicular to a central longitudinal axis X of the handle 76, and/or adhesives. The straight proximal portion 78 is coaxial with the central longitudinal axis X of handle 76, and the distal portion 80 is curved from the proximal portion 78. Shaft 68 has a central longitudinal axis, with a longitudinally straight axis portion along proximal portion 78 and a longitudinally curved axis portion along distal portion 80. The longitudinally straight axis portion is defined by axis X and the central longitudinal axes of shaft 68 and handle 76, respectively, are disposed in plane P4 as shown in FIG. 7.

The suture engaging member 74, which defines or forms a distal end of the suture passer 66, is preferably a closed loop or hook 84. The loop 84 is preferably formed at a distal end of a length of wire, and the shaft 68 is preferably hollow or tubular to receive the length of wire therein with the loop disposed externally of or protruding from the distal end 72 of shaft 68. In the case of suture passer 66, shaft 68 is hollow or tubular to define a passage entirely therethrough, and a length of wire is disposed in the passage of shaft 68 and extends the entire length of shaft 68, the wire having a distal end protruding from the distal end 72 and formed into the loop 84. The wire 74 is secured to the shaft 68 and/or to the handle 76. As shown in FIG. 7, the loop 84 defines a circular ring-shape circumscribing an opening 86, the ring-shape having an external diameter greater than the cross-sectional or diametric dimension of the passage of shaft 68. Since the wire extends the entire length of shaft 68, the wire has a curved distal portion following the curvature of distal portion 80. The loop 84 is disposed in a plane transverse to plane P4 and tangential to the longitudinally curved axis portion of the central longitudinal axis of shaft 68.

The handle 76 has a cylindrical section terminating proximally at a rounded rearward or proximal end and merging with a tapered forward section having a truncated conical configuration terminating distally at a planar forward wall 88 disposed perpendicular to the central longitudinal axis X' of the handle 76. The perpendicular distance from forward wall 88 to a plane P5 parallel to forward wall 88 and tangential to curved distal portion 80 defines a length for shaft 68 externally of handle 76. Handle 76 preferably has a knurled outer or external surface to facilitate grasping. According to a preferred embodiment, the handle 66 has a length of 3.60 to 3.66 inches and, preferably, 3.63 inches, the cylindrical section of handle 66 has an external diameter of 0.302 to 0.322 inch and, preferably, 0.312 inch, the external diameter of forward wall 88 is 0.120 to 0.130 inch and, preferably, 0.125 inch, the proximal extension 82 of shaft 68 extends into the handle 76 a depth or distance of 1.0 inch proximally of the forward wall 88, the handle 76 is made of white Delrin, a central longitudinal axis of pin 83 is located 0.850 inch proximally of forward wall 88, the pin 83 has a diameter of 0.015 inch and is made of stainless steel, the shaft 68 has an external diameter of 0.043 inch, the distal portion 80 has a radius of curvature of 0.187, the perpendicular distance between forward wall 88 and plane P5 is 1.250 inches, the shaft 68 is made of 19RW 304 stainless steel tubing, the wire 74 is made of 300 series stainless steel having a diameter of 0.013 inch, the circular ring-shape defined by the loop 84 has an external diameter of 0.072 to 0.078 inch and, preferably, 0.075 inch, the loop 84 protrudes from the shaft 68 a distance of 0.095 inch, and the distal end 72 is located a perpendicular distance of 0.260 inch from the central longitudinal axis X.

The suture passer 66 is used to grasp and manipulate a suture via engagement of the suture with the suture engaging member. FIG. 7 illustrates a suture 90 in the form of a continuous length of filamentous suture material extending through opening 86 such that the suture 90 can be manipulated via manual manipulation of the suture passer 66. An exemplary suture for use in the method of the present invention is a #2-0 polyethylene monofilament suture.

Drill guide 10 is used to form converging passages in bone to create a continuous tunnel in the bone and a bone bridge used to fixate soft tissue to the bone. The drill guide 10, the drill bit 52, the suture passer 66 and the suture 90 comprise a kit or system for fixating soft tissue to bone by suturing the soft tissue to a bone bridge created in the bone. The components of the kit or system can all be supplied in a single package or unit for ease of use. FIGS. 8–14 illustrate a procedure for fixating soft tissue to bone according to the present invention. As shown in FIG. 8, an incision N is made in soft anatomical tissue T to access bone B normally covered by soft tissue T. A surface S of the bone B is exposed and is marked to indicate selected locations or sites for drilling converging passages, respectively, in the bone, such sites being selected in accordance with the desired location or site on bone B for creation of a bone bridge to which soft tissue T is to be fixated. The bone surface S can be marked in a conventional manner, such as with a medical marker, to visually indicate the selected drilling locations or sites. The bone surface S can be prepared, if medically indicated, prior to formation of the bone bridge. For example, the bone B can be resected to form or to contour the bone surface S.

The drill guide 10 is grasped via the handle 14 and is positioned on the bone surface 8 in alignment with the selected locations or sites as shown in FIG. 8. The drill guide 10 is tapped into place on the bone surface S, such as with an implement used to apply a downwardly directed force on the end 44 of handle 14, causing the tips 46 of projections 16 to penetrate the bone B. The projections 16 will enter the bone B until the lowermost ends or contact points 39 of arch member 23 engage, contact or come into abutment with the bone surface S to prevent further penetration of the projections 16 into the bone B as shown in FIG. 9. Accordingly, the arch member 23 serves as a stop or abutment controlling or ensuring the depth of penetration of projections 16 below the bone surface S to a predetermined penetration depth. The drill guide 10 will then be in the proper position on the bone B and will be held and stabilized in such position due to engagement of projections 16 with the bone B as well as abutment of contact points 39 with bone surface S. The support plate 15 is supported above and spaced from the bone surface S by arch member 23, and a space or recess 89 is defined between the bottom wall 32 of the arch member and the bone surface S. Since the projections 16 penetrate the bone B less than the entire length of the projections, minimal force is needed when tapping the drill guide 10 in place on the bone, and only a minimal quantity of bone is displaced or removed. With the projections 16 penetrating the bone B to the predetermined depth, as controlled by the arch member 23, the point of convergence I will be disposed a predetermined depth within the bone B, i.e. below, beneath or internally of the bone surface S.

The drill bit 52 is coupled with a handpiece (not shown) for rotationally driving the drill bit 52. The cutting member 54 is introduced or inserted in the entry opening of one of the guide passages 18 and, while being rotated by the handpiece, is advanced forwardly or distally in the one guide passage 18 to exit the exit opening thereof and enter the bone B. The cutting member 54, as guided by the one guide passage 18, is advanced into the bone B until the shoulder 62 abuts the corresponding end wall segment 29 as shown in FIG. 9. Rotation of cutting member 54 causes the cutting edges to cut the bone B and form a first, cylindrical, angled passage 92 in the bone B, the passage 92 being shown in FIG. 10 following withdrawal of the drill bit 52 from the bone B and the guide passage 18. When the shoulder 62 abuts the end wall segment 29 during formation of first passage 92, the cutting member 54 and, therefore, the first passage 92, will extend to a point M of maximum depth in the bone B. The drill bit 52 is then withdrawn from the one guide passage 18, and the drilling procedure is repeated using the other guide passage 18 to form a second, cylindrical, angled passage 92 in the bone B. Bone fragments or debris generated by formation of the passages 92 and 92' may accumulate in space 89.

FIG. 10 illustrates bone B following formation of the first and second passages 92 and 92 and withdrawal of the drill bit 52 from the bone B. The first and second passages 92 and 92' have a cross-sectional or diametric dimension or size corresponding to the cross-sectional or diametric dimension or size of fluted segment 50. The passages 92 and 92 have central longitudinal axes, respectively, intersecting at the point of convergence I, and the passages 92 and 92 converge at point M, which is aligned with the central axis X and the point of convergence I, to form or define a continuous tunnel 94 in bone B. The convergence of passages 92 and 92 at point M is achieved by controlling the depth to which the cutting member 54 is allowed to enter the bone B, such depth being controlled, limited or determined by engagement of the shoulder 62 with the end wall segments 29 of the ridge member 21, so that the cutting member and the passages formed thereby do not "overshoot" or extend beyond point M. Accordingly, the ridge member 21 serves as a stop or abutment for the drill bit 52 to ensure that no more bone than necessary is removed when forming the tunnel 94.

Point M is located a predetermined shallow depth, approximately 4 mm for the preferred embodiment, in bone B, and the perpendicular distance from the lower surface 22 to point I is less than the perpendicular distance from the lower surface 22 to point M. Each passage 92 and 92 defines an access opening 96 and 96, respectively, on or along the bone surface S, the access openings 96 and 96 communicating with the tunnel 94. Formation of bone tunnel 94 results in creation of a bone bridge 97 between access openings 96 and 96. The bone bridge 97 defines an upper wall portion of bone tunnel 94 and is integrally connected to the remainder of bone B. As shown in FIG. 10, the bone bridge 97 has a triangular configuration in cross-section defining a corner 98 in tunnel 94.

Once the tunnel 94 and bone bridge 97 have been created in bone B, the drill guide 10 is removed from the bone. A bone rasp (not shown) is inserted in the tunnel 94 via one of the access openings 96 or 96 and is used to smooth or round the corner 98. FIG. 10 illustrates the corner 98 prior to being smoothed or rounded while FIG. 11, which shows bone B subsequent to removal of the drill guide 10, illustrates the corner 98 after being rounded or smoothed.

Figure 12:
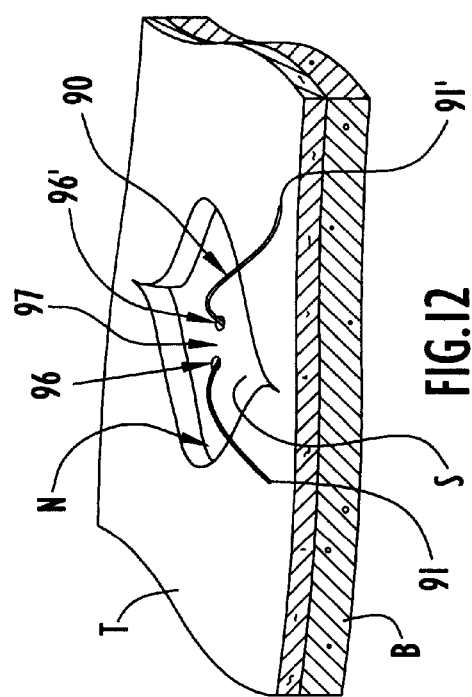
FIG. 12 is a broken view, partly in section, illustrating ends of the suture protruding externally from the access openings, respectively, upon withdrawal of the suture passer from the tunnel.
Figure 11:
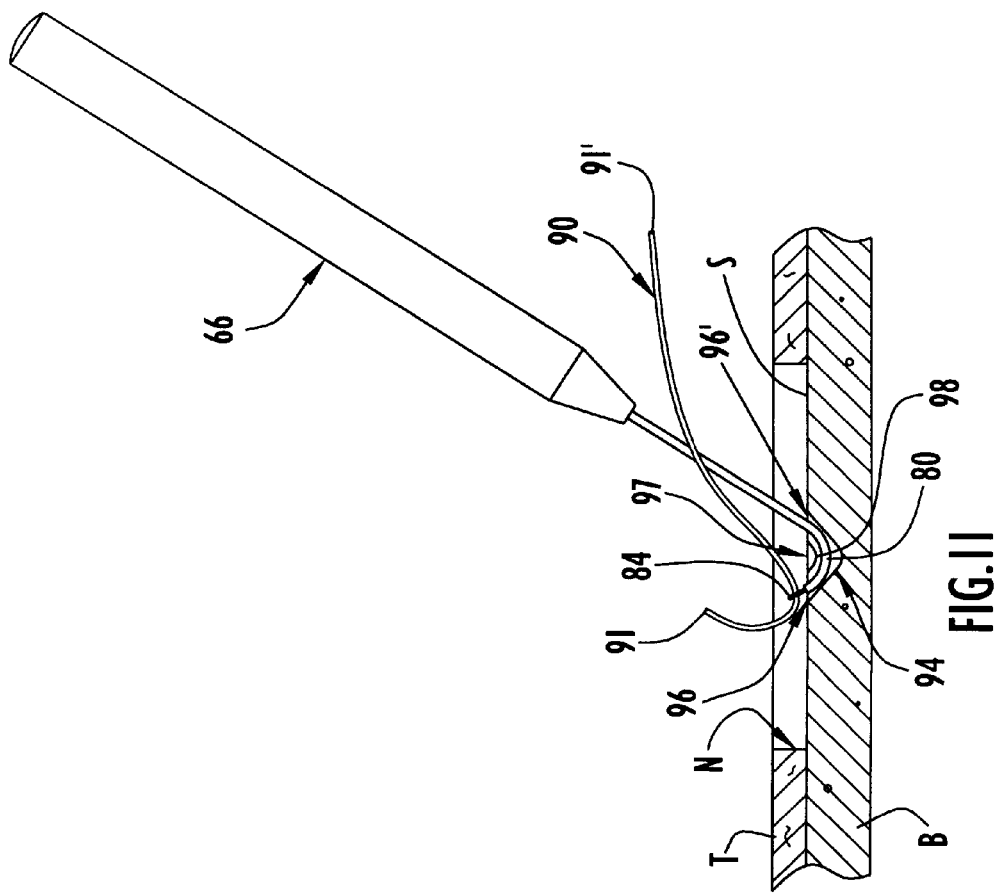
FIG. 11 is a broken view, partly in section, illustrating use of the suture passer to pass the suture through the tunnel.

The suture passer 66 is introduced, distal end first, in the tunnel 94 via one of the access openings 96 or 96 and is used to pass the suture 90 through the tunnel 94. FIG. 11 shows the curved portion 80 of suture passer 66 introduced in the bone tunnel 94 via the access opening 96 such that the distal end of the suture passer, i.e. loop 84, protrudes externally from the access opening 96. The suture 90, preferably a #2-0 polyethylene monofilament suture, is passed through the opening 86 of the loop 84, which protrudes above the bone surface S. The suture passer 66 is backed out of the bone tunnel 94 to be withdrawn from the bone tunnel 94 via the access opening 96, causing the suture 90 to be drawn or passed through the bone tunnel 94. To facilitate passage of the suture 90 through the bone tunnel 94, an end 91 of the suture 90 may be held or grasped externally of bone surface S as the suture passer 66 is backed out of the bone tunnel 94. Withdrawal of the suture passer 66 from the bone tunnel 94 results in an opposing end 91 of suture 90 being withdrawn from the bone tunnel 94 through access opening 96 such that the suture 90 extends entirely through the bone tunnel 94 with the end 91 exiting the bone tunnel 94 through access opening 96 and the end 91 exiting the bone tunnel 94 through access opening 96 as shown in FIG. 12.

The suture 90 is passed through soft anatomical tissue and is tied or knotted to secure the soft anatomical tissue to the bone B with desired tension. In the illustrated procedure, one of the ends 91 or 91 of suture 90 is passed through the tissue T on both sides of the anterior aspect of the previously formed incision N. As shown in FIG. 13, end 91 of suture 90 is passed through a tissue portion 95 of tissue T disposed anteriorly and on one side of the incision N and through a tissue portion 95' of tissue T disposed anteriorly but on an opposite side of the incision N. The ends 91 and 91 of suture 90 are tied or knotted, and the suture 90 is pulled or tightened to secure the tissue T to the bone B with desired tension. Accordingly, the tissue T is fixated to the bone bridge 97. By suturing the tissue T at the anterior aspect and tensioning the suture 90, the tissue T can be lifted or elevated relative to the bone, as shown in FIG. 14, and then fixated in the lifted or elevated position as is particularly useful in cosmetic surgery. The extent to which the tissue T is lifted or elevated can be controlled or adjusted through selection of the suturing site on tissue T and control of the suture tension. The ends 91 and 91 of suture 90 can be trimmed, as necessary, thusly completing the soft tissue fixation procedure. It should be appreciated that the suture 90 can be passed through the tissue T with the use of a suture needle (not shown) in a conventional manner.

The present invention allows a shallow bone tunnel to be formed in bone to a maximum predetermined depth to create a bone bridge in the bone about which a suture passed through the bone tunnel and through soft tissue can be secured to fixate the soft tissue to the bone with desired tension. With the present invention, soft tissue is reliably and effectively fixated to bone while eliminating the need for temporary or permanent mechanical fixation devices, enhancing patient comfort and confidence and reducing surgical cost. The present invention is applicable to many areas of surgery and is particularly useful in cosmetic surgery, especially in brow elevation procedures.

In as much as the present invention is subject to many variations, modifications and changes in detail, it is intended that all subject matter discussed above or shown in the accompanying drawings be interpreted as illustrative only and not be taken in a limiting sense.

What is claimed is:

1. A drill guide for use in forming converging passages in bone cooperating to form a continuous tunnel in the bone comprising a guide member for positioning upon a surface of a bone and including a support plate, an abutment member protruding below said support plate and forming a contact point for abutment with the surface of the bone, a projection protruding below said support plate and terminating at a tip disposed a predetermined distance below said support plate for penetrating the bone, said contact point being disposed a predetermined distance below said support plate that is less than said predetermined distance that said tip is disposed below said support plate such that said projection penetrates the bone to a predetermined depth when said contact point is in abutment with the surface of the bone; and a pair of guide passages extending angularly, entirely through said guide member for receiving and guiding a drill bit, said guide passages having central longitudinal axes, respectively, converging at a predetermined point within the bone when said projection penetrates the bone to said predetermined depth such that a drill bit guided into the bone by said guide passage forms converging passages in the bone cooperating to form a continuous tunnel in the bone.

2. A drill guide as recited in claim 1 wherein said support plate includes a planar upper surface, a planar lower surface and a uniform thickness between said upper and lower surfaces, and said abutment member protrudes downwardly from said lower surface.

3. A drill guide as recited in claim 2 wherein said guide member includes a plurality of projections extending perpendicularly from said lower surface, each of said projections terminating at a tip disposed said predetermined distance below said lower surface for penetrating the bone.

4. A drill guide as recited in claim 3 wherein said abutment member forms a pair of contact points disposed said predetermined distance below said lower surface that is less than said predetermined distance that said tips are disposed below said lower surface, and said guide passages have exit openings, respectively, disposed on said abutment member adjacent said contact points, respectively.

5. A drill guide as recited in claim 4 wherein said central longitudinal axes of said guide passages are disposed at an angle of 40 to said upper surface.

6. A drill guide as recited in claim 5 wherein said support plate includes a central axis and said plurality of projections includes three projections arranged in a triangular pattern around said central axis of said support plate.

7. A drill guide as recited in claim 6 wherein said guide member further includes a ridge member protruding upwardly from said upper surface and said guide passages have entry openings, respectively, on said ridge member, said ridge member forming a stop ensuring insertion of a drill bit in said guide passages, via said entry openings, to a predetermined depth.

8. A drill guide as recited in claim 7 wherein said abutment member includes a bottom wall extending between said contact points and configured to define a space between said bottom wall and the surface of the bone when said contact points are in abutment with the surface of the bone.

9. A drill guide as recited in claim 8 and further including a handle extending upwardly from said ridge member in alignment with said central axis of said support plate.

10. A kit for fixating soft tissue to bone comprising a drill guide including a guide member for positioning upon a surface of a bone and comprising a support plate, an abutment member terminating below said support plate at a contact point forming an abutment with the surface of the bone when said guide member is positioned thereupon, a projection terminating below said support plate at a tip disposed a predetermined distance below said support plate for penetrating the bone and a pair of guide passages extending angularly, entirely through said guide member, said contact point being disposed a predetermined distance below said support plate that is less than said predetermined distance that said tip is disposed below said support plate such that said projection penetrates the bone to a predetermined depth when said contact point is in abutment with the surface of the bone, said guide passages having central longitudinal axes, respectively, converging at a predetermined point within the bone when said projection penetrates the bone to said predetermined depth;

a drill bit including a cutting member for being introduced in said guide passages and for being moved forwardly in said guide passages into the bone to cut converging passages, respectively, in the bone forming a continuous tunnel in the bone having access openings, respectively, on the surface of the bone;

a suture for being passed through the tunnel and comprising a length of filamentous suture material terminating at opposing ends; and a suture passer for passing said suture through the tunnel, said suture passer having a portion for being introduced in the tunnel through one of the access openings and a suture engaging member for protruding externally from the tunnel through the other of the access openings for engaging said suture externally of the bone such that said suture is passed through the tunnel when said suture passer is withdrawn from the tunnel through the one access opening whereby said suture extends entirely through the tunnel with said opposing ends extending through the access openings, respectively, for suturing soft tissue to the bone.

11. A kit for fixating soft tissue to bone as recited in claim 10 and further including a stop on said drill bit engageable with said guide member to ensure movement of said cutting member into the bone to a maximum predetermined depth.

12. A kit for fixating soft tissue to bone as recited in claim 11 wherein said guide member further includes a ridge member protruding above said support plate and said stop includes a shoulder on said drill bit for abutting said ridge member.

13. A kit for fixating soft tissue to bone as recited in claim 12 wherein said suture engaging member includes a loop circumscribing an opening for receiving said suture therethrough.

14. A method of fixating soft tissue to bone comprising the steps of positioning a drill guide upon a surface of a bone to which soft tissue is to be fixated;

penetrating the bone with a projection of the drill guide;

engaging the surface of the bone with an abutment of the drill guide to ensure penetration of the bone by the projection to a predetermined depth, less than the length of the projection, such that central longitudinal axes of guide passages, respectively, of the drill guide converge at a predetermined point within the bone;

introducing a drill bit through one of the guide passages and into the bone to form a first passage in the bone;

withdrawing the drill bit from the one guide passage;

introducing the drill bit through the other guide passage and into the bone to form a second passage in the bone converging with the first passage to define a continuous tunnel in the bone having access openings, respectively, on the surface of the bone and a bone bridge between the access openings;

withdrawing the drill bit from the other guide passage;

introducing a portion of a suture passer into the tunnel through one of the access openings such that a suture engaging member of the suture passer protrudes externally from the tunnel through the other access opening;

engaging a filamentous suture with the suture engaging member externally of the bone;

withdrawing the suture passer from the tunnel through the one access opening to draw the suture through the tunnel such that the suture extends entirely through the tunnel with opposing ends of the suture extending externally of the bone through the access openings, respectively;

passing one of the ends of the suture through soft tissue; and tying the ends of the suture to fixate the soft tissue to the bone bridge.

15. A method of fixating soft tissue to bone as recited in claim 14 wherein said step of penetrating includes penetrating the bone with sharp tips of three projections, respectively, of the drill guide.

16. A method of fixating soft tissue to bone as recited in claim 15 wherein said step of engaging the surface of the bone includes engaging the surface of the bone with a pair of contact points of the abutment member.

17. A method of fixating soft tissue to bone as recited in claim 16 wherein said steps of introducing a drill bit include engaging the drill guide with a stop on the drill bit to prevent movement of the drill bit into the bone beyond a maximum predetermined depth such that the first and second passages converge at a predetermined point in the bone.

18. A method of fixating soft tissue to bone as recited in claim 17 wherein said step of engaging the drill guide includes engaging a ridge member of the drill guide with a shoulder of the drill bit.

19. A method of fixating soft tissue to bone as recited in claim 18 wherein said steps of introducing a drill bit include forming the first and second passages to converge at a predetermined point located a depth of 4 mm in the bone.

20. A method of fixating soft tissue to bone as recited in claim 19 wherein said step of tying includes tensioning the suture to elevate the soft tissue relative to the bone and fixating the soft tissue in the elevated position.

* * * * *